United States Patent [19]
Ward et al.

[11] Patent Number: 5,610,060
[45] Date of Patent: Mar. 11, 1997

[54] ISOLATED *HELICOBACTER HEPATICUS*

[75] Inventors: Jerrold M. Ward, Gaithersburg, Md.;
James G. Fox, Harvard, Mass.;
Michael J. Collins, Jr., Laurel, Md.;
Peter L. Gorelick, Frederick, Md.;
Raoul E. Benveniste, Bethesda, Md.;
Joseph G. Tully, Germantown, Md.;
Matthew A. Gonda, Walkersville, Md.;
Bruce J. Paster, Lee, N.H.; Floyd E. Dewhirst, III, Medfield, Mass.

[73] Assignee: The United States of America as represented by the Department of Health and Human Services, Washington, D.C.

[21] Appl. No.: 266,414

[22] Filed: Jun. 24, 1994

[51] Int. Cl.$^6$ ................................................ C12N 1/20
[52] U.S. Cl. ............................... 435/252.1; 435/243
[58] Field of Search ........................................ 435/252.1

[56] References Cited

U.S. PATENT DOCUMENTS 5,411,948  5/1995  Lingwood et al. ........................ 514/78

OTHER PUBLICATIONS

Fox et al., J. Clin Microb., May 1994, pp. 1238–1245.
Battles et al., J. Clin. Microb., May 1995, pp. 1344–1347.
Wotherspoon et al. *Lancet* 342:575–577 (1993).
Stanley et al. *J. Gen. Microbiol.* 139:2495–2504 (1993).
Eaton et al. *Int. J. Sys. Bacteriol.* 43:99–106 (1993).
V.J. Desmet, *In Oxford Textbook of Pathology*, J.O.P. McGee, P.G. Isaacson, and N.S. Wright, Eds. Oxford Univ. Press, Oxford, pp. 1312–1324 (1992).
M. J. Blaser, *Clin. Inf. Dis.* 15, 386 (1992).
Kita et al. *J. Med. Microbiol.* 37, 326–331 (1992).
Nomura et al. *New Engl. J. Med.* 325:1132–1136 (1991).
Parsonnet et al. *New Engl. J. Med.* 325:1127–1131 (1991).
Bronsdon et al. *Intl. J. Syst. Bacteriol.* 41(1):148–153 (1991).
Kita, et al., *J. Med. Microbiol.* 33, 171 (1990).
Lee et al. *Infect. Immun.* 56:2843–2850 (1988).
Kita, et al, *J. Gen. Microbiol.* 132, 3095. (1986).
Fox et al. *Am. J. Vet. Res.* 47:236–239 (1986).
Totten et al. *J. Infect. Diseases* 151:131–139 (1985).
Fennell et al. *J. Infect. Dis.* 149:58–66 (1984).
Marshall et al. *Lancet* i:1311–1314 (1984).
Reddy et al. *J. Clin. Gastroenterol.* 5, 259 (1983).

*Primary Examiner*—John W. Rollins
*Assistant Examiner*—Deborah Ware
*Attorney, Agent, or Firm*—Needle & Rosenberg, P.C.

[57] ABSTRACT

An isolated bacterium of the genus Helicobacter, characterized by the 16S ribosomal RNA encoding nucleotide sequence defined in the Sequence Listing as SEQ ID NO:1 is provided. An isolated nucleic acid having the nucleotide sequence defined in the Sequence Listing as SEQ ID NO:1 is provided. Such a nucleic acid can be used for diagnosis of infection with *H. hepaticus*. A nucleic acid of the present invention in a vector suitable for expression of the nucleic acid is also provided. The vector can be in a host suitable for expressing the nucleic acid. A purified antigen specific for *H. hepaticus* is provided. A method of making an animal model for chronic Helicobacter infection is also provided.

1 Claim, No Drawings

SEQUENCE LISTING ( 1 ) GENERAL INFORMATION:

( i i i ) NUMBER OF SEQUENCES: 9

( 2 ) INFORMATION FOR SEQ ID NO:1:

( i ) SEQUENCE CHARACTERISTICS:
    ( A ) LENGTH: 1420 base pairs
    ( B ) TYPE: nucleic acid
    ( C ) STRANDEDNESS: single
    ( D ) TOPOLOGY: linear ( i i ) MOLECULE TYPE: ribosomal RNA ( x i ) SEQUENCE DESCRIPTION: SEQ ID NO:1:

```
CAGAGUGAAC  GCUGGCGGCG  UGCCUAAUAC  AUGCAAGUCG  AACGAUGAAU  CUUCUAGCUU    60
GCUAGAAGUG  GAUUAGUGGC  GCACGGGUGA  GUAAUGCAUA  GGUUAUGUGC  CCUUUAGUCU   120
GGGAUAGCCA  CUGGAAACGG  UGAUUAAUAC  UGGAUACUCC  CUACGGGGGA  AAGUUUUCG    180
CUAAAGGAUC  AGCCUAUGUC  CUAUCAGCUU  GUUGGUGAGG  UAAUGGCUCA  CCAAGGCUAU   240
GACGGGUAUC  CGGCCUGAGA  GGGUGAUCGG  ACACACUGGA  ACUGAGACAC  GGUCCAGACU   300
CCUACGGGAG  GCAGCAGUAG  GGAAUAUUGC  UCAAUGGGGG  AAACCCUGAA  GCAGCAACGC   360
CGCGUGGAGG  AUGAAGGUUU  UAGGAUUGUA  AACUCCUUUU  GUUAGAGAAG  AUUAUGACGG   420
UAUCUAACGA  AUAAGCACCG  GCUAACUCCG  UGCCAGCAGC  CGCGGUAAUA  CGGAGGGUGC   480
AAGCGUUACU  CGGAAUCACU  GGGCGUAAAG  AGUGCGUAGG  CGGGGUAAUA  AGUCAGAUGU   540
GAAAUCCUGU  AGCUUAACUA  CAGAACUGCA  UUUGAAACUG  UUACUCUGGA  GUGUGGGAGA   600
GGUAGGUGGA  AUUCUUGGUG  UAGGGUAAA   AUCCGUAGAG  AUCAAGAGGA  AUACUCAUUG   660
CGAAGGCGAC  CUGCUGGAAC  AUUACUGACG  CUGAUGCACG  AAAGCGUGGG  GAGCAAACAG   720
GAUUAGAUAC  CCUGGUAGUC  CACGCCCUAA  ACGAUGGAUG  CUAGUUGUUG  CCUUGCUUGU   780
CAGGGCAGUA  AUGCAGCUAA  CGCAUUAAGC  AUCCCGCCUG  GGGAGUACGG  UCGCAAGAUU   840
AAAACUCAAA  GGAAUAGACG  GGACCCGCA   CAAGCGGUGG  AGCAUGUGGU  UUAAUUCGAA   900
GAUACGCGAA  GAACCUUACC  UAGGCUUGAC  AUUGAUAGAA  UCUACUAGAG  AUAGUGGAGU   960
GCCUUCGGGG  AGCUUGAAAA  CAGGUGCUGC  ACGGCUGUCG  UCAGCUCGUG  UCGUGAGAUG  1020
UUGGGUUAAG  UCCCGCAACG  AGCGCAACCC  UCGUCCUUAG  UUGCUAGCAG  UUCGGCUGAG  1080
CACUCUAAGG  AGACUGCCUU  CGUAAGGAGG  AGGAAGGUGA  GGACGACGUC  AAGUCAUCAU  1140
GGCCCUUACG  CCUAGGGCUA  CACACGUGCU  ACAAUGGGGC  GCACAAAGAG  GAGCAAUAUC  1200
GCGAGGUGGA  GCAAAUCUCA  AAAACGUCUC  UCAGUUCGGA  UUGUAGUCUG  CAACUCGACU  1260
ACAUGAAGCU  GGAAUCGCUA  GUAAUCGUGA  AUCAGCCAUG  UCACGGUGAA  UACGUUCCCG  1320
GGUUUGUACU  CACCGCCCGU  CACACCAUGG  GAGUUGUAUU  CGCCUUAAGU  CGGGAUACUA  1380
AAUUGGUUAC  CGCCCACGGC  GGAUGCAGCG  ACUGGGGUGA                          1420
```

( 2 ) INFORMATION FOR SEQ ID NO:2:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( i i ) MOLECULE TYPE: oligonucleotide ( x i ) SEQUENCE DESCRIPTION: SEQ ID NO:2:

```
AGAGTTYGAT  YCTGGCT                                                       17
```

( 2 ) INFORMATION FOR SEQ ID NO:3:

( i ) SEQUENCE CHARACTERISTICS:
        ( A ) LENGTH: 21 base pairs
        ( B ) TYPE: nucleic acid
        ( C ) STRANDEDNESS: single (D) TOPOLOGY: linear (ii) MOLECULE TYPE: oligonucleotide (xi) SEQUENCE DESCRIPTION: SEQ ID NO:3:

TACGGYTACC TTGTTACGAC T　　　　　　　　　　　　　　　　　　　　　　　21

(2) INFORMATION FOR SEQ ID NO:4:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: oligonucleotide (xi) SEQUENCE DESCRIPTION: SEQ ID NO:4:

GGAATCGCTA GTAATCG　　　　　　　　　　　　　　　　　　　　　　　　　17

(2) INFORMATION FOR SEQ ID NO:5:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (ii) MOLECULE TYPE: oligonucleotide (xi) SEQUENCE DESCRIPTION: SEQ ID NO:5:

ACTGCTGCCT CCCGT　　　　　　　　　　　　　　　　　　　　　　　　　　15

(2) INFORMATION FOR SEQ ID NO:6:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: oligonucleotide (xi) SEQUENCE DESCRIPTION: SEQ ID NO:6:

GTRTTACCGC GGCTGCTG　　　　　　　　　　　　　　　　　　　　　　　　18

(2) INFORMATION FOR SEQ ID NO:7:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: oligonucleotide (xi) SEQUENCE DESCRIPTION: SEQ ID NO:7:

CTACCAGGGT ATCTAATC　　　　　　　　　　　　　　　　　　　　　　　　18

(2) INFORMATION FOR SEQ ID NO:8:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: oligonucleotide (xi) SEQUENCE DESCRIPTION: SEQ ID NO:8:

```
GGTTGCGCTC GTTGCGGG                                                              18
```

( 2 ) INFORMATION FOR SEQ ID NO:9:

( i ) SEQUENCE CHARACTERISTICS:
        ( A ) LENGTH: 19 base pairs
        ( B ) TYPE: nucleic acid
        ( C ) STRANDEDNESS: single
        ( D ) TOPOLOGY: linear ( i i ) MOLECULE TYPE: oligonucleotide ( x i ) SEQUENCE DESCRIPTION: SEQ ID NO:9:

```
CCCGGGAACG TATTCACCG                                                             19
```

ISOLATED *HELICOBACTER HEPATICUS*

This invention was made with government support under PHS Contract N01-C0-74102 with Program Resources, Inc./ Dyn Corp.; and PHS Grants RRO 1046 awarded by he Center for Research Resources, National Institutes of Health; PO1-CA26731 from the National Cancer Institute; DE 10374 from the National Institute of Dental Research; DE-04881 and DE-08303 from the National Institute of Dental Research; and RR-01046 and RR-07036 from the National Center for Research Resources and NCI contract RFPS94-69. The government has certain rights in the invention.

BACKGROUND OF THE INVENTION

During the last decade microaerophilic spiral to curved shape bacteria isolated from the stomach of humans and animals have been the focus of considerable research because of their association with gastric disease (32). These microorganisms are now recognized as belonging to the genus Helicobacter. It is now known that the species *Helicobacter pylori* causes active, chronic gastritis and peptic ulcer disease in humans (1,25,32). This microorganism has also been recently linked to the development of gastric adenocarcinoma and gastric mucosal associated lymphoma (22,33,35,47). Several additional species of Helicobacter that have been isolated from the stomachs of various mammalian species (13,16,23,31) and have been shown to cause varying degrees of gastritis in their hosts (20,21,24). Additional species of Helicobacter have been isolated from the intestinal tracts of mammals (1,17,42,44) and birds (15). One of these, *H. muridarum* primarily colonizes the ileum and cecum of rodents, but can also apparently elicit a gastritis after colonizing the gastric mucosa of older rodents (1,2). Also, "*Helicobacter (Flexispira) rappini*" has been associated with abortion in sheep and intestinal disease in animals and humans (12,27,39). Most recently "*H. rappini*" has been isolated from the colon and cecum of mice (41).

Helicobacter species are often commensal bacteria in the gastrointestinal tract or are associated with chronic diseases in humans and animals (1). In humans, *H. pylori* has been associated with chronic, active gastritis, peptic ulcer and gastric carcinoma. Other Helicobacter organisms cause gastritis naturally in ferrets (*H. mustelae*), dogs and cats (*H. fells*) and cheetahs, (*H. acinoynx*) (2). Helicobacter species colonizing the lower GI tract of mice and causing no apparent disease include *H. muridarum* and "*H. rappini*", although *H. muridarum* can under certain conditions also colonize the stomach of mice and induce gastritis (2).

*Campylobacter jejuni* infections have been associated with rare hepatitis in humans (8) and in mice experimentally inoculated with selected strains of *C. jejuni* (9). Chronic active hepatitis in humans (10) and dogs (11) is sometimes caused by Leptospires.

The present invention provides the discovery of a novel species of Helicobacter (*Helicobacter hepaticus*) that colonizes experimental mice. The prevalence of this Helicobacter infection in experimental research colonies throughout the United States is not known. It is possible, because of shipment of mice to other facilities over the past two years, that infected mice may have been distributed elsewhere. The potential complications to research by this insidious chronic infection are significant. No routine serologic test is available at present to diagnose this infection. Because this infection produces no clinical signs and may only be apparent in older mice, it is of utmost importance to screen mouse colonies by serology and histologic examination of liver sections for these organisms. Thus, methods for diagnosing *Helicobacter hepaticus* infection are provided.

SUMMARY OF THE INVENTION

An isolated *Helicobacter hepaticus* bacterium is provided. An isolated bacterium of the genus Helicobacter that induces the formation of hepatic tumors in mammals is also provided. An isolated bacterium of the genus Helicobacter, characterized by the 16S ribosomal RNA having the nucleotide sequence defined in the Sequence Listing as SEQ ID NO:1 is provided.

An isolated nucleic acid encoding the 16S ribosomal RNA having the nucleotide sequence defined in the Sequence Listing as SEQ ID NO:1 is provided. This is a unique 16S rDNA fragment of *H. hepaticus*. Such a nucleic acid can be used for diagnosis of infection with *H. hepaticus*. A nucleic acid of the present invention in a vector suitable for expression of the nucleic acid is also provided. The vector can be in a host suitable for expressing the nucleic acid.

A purified antigen specific for *H. hepaticus* is provided. The antigen can be the whole purified organism or it can be a specific antigenic fragment of the organism. The antigen can be used in the immunodiagnostic methods or vaccines as described below.

A method of making an animal model for chronic Helicobacter infection is also provided. The method can comprise administering to an animal an infectious amount of *H. hepaticus*, the resulting infected animal being a model for Helicobacter infection. The animal can be a mouse.

DETAILED DESCRIPTION OF THE INVENTION

Isolated *Helicobacter hepaticus*

An isolated *H. hepaticus* bacterium is provided. An example of an isolated *H. hepaticus* bacterium is characterized by the 16S ribosomal RNA having the nucleotide sequence defined in the Sequence Listing as SEQ ID NO:1 is provided. "Isolated" is defined as a bacterial preparation that is separated from other bacterial and cellular contaminants normally found in its natural environment, e.g., the gastrointestinal tract. This bacterial preparation is contemplated to be sufficiently separated from other bacterial and cellular contaminants to be acceptable for use in a therapeutic, diagnostic or research setting. For example, a *H. hepaticus* preparation that has been sufficiently separated from other bacterial and cellular contaminants so that it is useful in a diagnostic assay, such as an ELISA or Western blot, is "isolated." Specific examples of isolation procedures are provided in the Examples.

As will be seen below in the Examples, there are other defining characteristics which distinguish the present *H. hepaticus* from other Helicobacter species. Other isolates of this organism from different hosts, for example, isolates from humans, fall within the scope of this invention. Thus, *H. hepaticus* having minor nucleotide variations such that the bacterium would still be classified as *H. hepaticus* are provided. These variants can be identified by following the isolation and characterization procedures set forth herein.

Whether a bacterium is of the *H. hepaticus* species can be ascertained by number of methods which are known in the art and described herein. Thus, any of the distinguishing characteristics of the present species, provided in the Examples or later determined, can be used to identify other isolates that fall within the species.

Because the bacterium of the present invention induces hepatitis and hepatic tumors, the invention provides an isolated bacterium of the genus Helicobacter that induces the formation of hepatic tumors in mammals. The novel Helicobacter bacterium may also induce other tumors of the gastrointestinal tract, distinguishable from gastric tumors induced by *Helicobacter pylori*. These tumor-inducing Helicobacter can be used to develop diagnostic and treatment reagents, and methods, such as those described below.

A nonpathogenic *H. hepaticus* antigen can be derived by modifying the *H. hepaticus* organism using standard techniques. For example, the whole cell antigen can be subjected to gamma irradiation to render the *H. hepaticus* nonpathogenic. Other standard methods of inactivating whole cell antigen include treatment with β-propriolactone or formalin (48). The pathogenicity the modified organism can be tested in a mouse model by comparison to a known-pathogenic isolate. These and other methods of generating nonpathogenic bacteria can be applied to generate a nonpathogenic tumor-inducing Helicobacter as well.

Purified Antigen

A purified antigen specific for *H. hepaticus* is provided. A purified antigen specific for the tumor-inducing Helicobacter of the invention is also provided. As used herein, "purified" means the antigen is contemplated to be sufficiently separated from other bacterial and cellular contaminants to be acceptable for use in a therapeutic, diagnostic or research setting. For example, a *H. hepaticus* antigen preparation that has been sufficiently separated from other bacterial and cellular contaminants so that it is useful in a diagnostic assay, such as an ELISA or Western blot, is "purified." Specific examples of purification procedures are provided and otherwise well-known in the art. The antigen can be the whole purified organism or it can be a specific antigenic fragment (protein or polypeptide) of the organism. An antigenic fragment can be isolated from the whole antigen by chemical or mechanical disruption. The purified fragments thus obtained can be tested to determine their immunoreactivity and specificity by routine methods. Antigenic fragments of the antigen can also be synthesized directly. An immunoreactive fragment is defined as an amino acid sequence of at least about 5 consecutive amino acids derived from the antigen amino acid sequence.

Alternatively, a protein moiety of *H. hepaticus* can be obtained by treating the whole organism with an ionic detergent such as sodium dodecyl sulfate or a nonionic detergent such as Triton X-100 ($C_{34}H_6O_{11}$ average) or ethylphenyl-polyethylene glycol (NP-40, Shell Oil Company). The protein fragments so obtained can be tested for immunoreactivity and specificity as described above. Other immunogenically specific determinants of *H. hepaticus* can be obtained by the standard methods described above.

The antigenically specific determinant of this invention can be obtained by synthesizing a vector comprising a nucleic acid sequence encoding an antigenically specific determinant of *H. hepaticus*. The vector can then be placed in a host wherein the antigenically specific determinant of *H. hepaticus* will be synthesized. The selection of a nucleic acid sequence that encodes an antigenically specific determinant can be accomplished by screening clone libraries of *H. hepaticus* DNA. Briefly, the *H. hepaticus* is lysed and the DNA extracted via standard procedure using 1% sodium dodecyl sulfate and proteinase K. The resulting DNA is then partially digested with restriction endonuclease EcoRI, size fractionated and gel purified (agarose gel electrophoresis), and cloned into lambda phage vector lambda zapII following standard procedures such as described in Sambrook et al. (49). The recombinant plaques are screened for antigen production via ELISA with primary antibody being human or other non-human (e.g., mouse) convalescent sera absorbed with an *E. coli* lysate. Antigen expressing clones are subcloned.

The subclones expressing *H. hepaticus* specific antigens are sequenced and corresponding synthetic peptides are constructed from the deduced amino acid sequence for use as diagnostic antigens or immunogens. Alternatively, recombinant antigens could be purified by affinity chromatography or high pressure liquid chromatography and the like.

Vaccines

The nonpathogenic *H. hepaticus* antigen of this invention can be used in the construction of a vaccine comprising an immunogenic amount of *H. hepaticus* antigen and a pharmaceutically acceptable carrier. This *H. hepaticus* antigen can be killed or modified live *H. hepaticus* or immunogenic fragments of *H. hepaticus*. Alternatively, mixtures of intact nonpathogenic *H. hepaticus* and immunogenic fragments can be used. The vaccine can then be used in a method of preventing infection in a subject by administering the vaccine to the subject. The nonpathogenic tumor-inducing Helicobacter, or antigen specific for the Helicobacter can also be used in a vaccine as described herein. Thus, diseases associated with *H. hepaticus* or other tumor-inducing Helicobacter infections can be prevented by use of the vaccines of this invention. The prevention methods will work when the subject is a human, or likewise when the subject is a nonhuman animal, such as a mouse.

The antigen to be used in the vaccine can be tested to determine its protective ability and specificity. Briefly, various concentrations of a putative immunogenically specific fragment are prepared and administered to an animal and the immunological response (e.g., the production of antibodies or cell mediated immunity) of an animal to each concentration is determined. The amounts of antigen administered depend on the subject, e.g. a human, a guinea pig or a mouse, the condition of the subject, the size of the subject, etc. Thereafter, an animal so inoculated with the antigen can be exposed to the bacterium to test the protective effect of the specific immunogenic fragment. The specificity of a putative immunogenic fragment can be ascertained by testing sera, other fluids or lymphocytes from the inoculated animal for cross reactivity with other closely related bacteria.

The pharmaceutically acceptable carrier in the vaccine of the instant invention can comprise saline or other suitable carriers (50). An adjuvant can also be a part of the carrier of the vaccine, in which case it can be selected by standard criteria based on the particular *H. hepaticus* antigen used, the mode of administration and the subject (50). Methods of administration can be by oral or sublingual means, or by injection, depending on the particular vaccine used and the subject to whom it is administered.

It can be appreciated from the above that the vaccine can be used as a prophylactic or a therapeutic. Thus, subjects with the disease can be treated utilizing the vaccine. Further, through such vaccination the spread of disease between animals and humans can be prevented.

Purified Antibodies

A purified antibody that specifically binds the antigen is also provided. The antibody can bind the intact *H. hepaticus* or tumor-inducing Helicobacter or antigenic fragments thereof. The antibodies can specifically bind a unique epitope of the antigen or they can also bind epitopes of other organisms. The antibody can be monoclonal or polyclonal. The term "bind" means the well understood antigen-antibody interaction or other nonrandom associations with an antigen. "Specifically binds" as used herein describes an antibody or other ligand that does not cross react substantially with any antigen other than the one specified, in this case, the *H. hepaticus* antigen.

Antibodies can be made as described in the published literature (see, for example, Harlow and Lane (48)). Briefly purified antigen can be injected into an animal in an amount and in intervals sufficient to elicit an immune response. Antibodies can either be purified directly, or spleen cells can be obtained from the animal. The cells are then fused with an immortal cell line and screened for antibody secretion. The antibodies can be used to screen DNA clone libraries for cells secreting the antigen. Those positive clones can then be sequenced by any of the well known methods (see, for example, Kelly et al. (51).

The antibody can be attached to a substrate or labeled with a detectable moiety or both immobilized and labeled. The detectable moieties contemplated with the composition of the present invention are those well known to the skilled practitioner, including fluorescent, enzymatic and radioactive markers.

Serological Detection (Diagnosis) Methods Detecting Antibody with Antigen

The present invention provides a method of detecting present or past *H. hepaticus* infection in a subject, comprising: (a) contacting the purified bacterium or specific antigen of the invention with an antibody-containing sample from the subject under conditions that permit an antibody-antigen binding reaction; and (b) detecting the reaction of the antibody with the bacterium, the presence of a reaction indicating present or past infection of the subject with the bacterium. As can be appreciated, this method can be routinely adapted to detect infection with the tumor-inducing Helicobacters of the invention.

In the diagnostic methods taught herein, the antigen can be bound to a substrate and contacted by a specimen such as feces, gastric secretions, serum, urine, saliva or other fluid. In this manner, antibodies specific for the antigen (the primary antibody) will specifically bind the immobilized antigen. Thereafter, a secondary antibody bound to, or labeled with, a detectable moiety can be added to enhance the detection of the primary antibody. Generally, the secondary antibody or other ligand which binds specifically with a different epitope of the antigen or nonspecifically with the ligand or reacted antibody, will be selected for its ability to react with multiple sites on the primary antibody. Thus, for example, several molecules of the secondary antibody can react with each primary antibody, making the primary antibody more detectable.

Detecting Antigen with Antibody

Also provided is a method for detecting present or past infection in a subject with *H. hepaticus* comprising (a) contacting a purified antibody that specifically binds *H. hepaticus* with an antigen-containing sample from the subject under conditions that permit an antigen/antibody binding reaction and (b) detecting the reaction of the antibody with the bacterium, the presence of a reaction indicating present or past infection of the subject with the bacterium.

It is contemplated that the epitope (antigen) with which the antibody reacts will be on intact cells, or will be antigenic fragments of the bacterium. As contemplated herein, the antibody includes any ligand which binds the antigen, for example, an intact antibody, a fragment of an antibody or another reagent that has reactivity with the antigen. The fluid sample of this method can comprise any body fluid which would contain the antigen or a cell containing the antigen, such as blood, plasma, serum, saliva and urine. Other possible examples of body fluids include sputum, mucus, gastric juice and the like.

ELISA

Enzyme immunoassays such as immunofluorescence assays (IFA), enzyme linked immunosorbent assays (ELISA) and immunoblotting can be readily adapted to accomplish the detection of the antigen. An ELISA method effective for the detection of the antigen can, for example, be as follows: (1) bind the antibody to a substrate; (2) contact the bound antibody with a fluid or tissue sample containing the antigen; (3) contact the above with a secondary antibody bound to a detectable moiety (e.g., horseradish peroxidase enzyme or alkaline phosphatase enzyme); (4) contact the above with the substrate for the enzyme; (5) contact the above with a color reagent; (6) observe color change. The above method can be readily modified to detect antibody as well as antigen.

Competitive Inhibition Assay

Another immunologic technique that can be useful in the detection of *H. hepaticus* or previous *H. hepaticus* infection utilizes monoclonal antibodies (MAbs) for detection of antibodies specifically reactive with the bacterium. Briefly, sera or other body fluids from the subject is reacted with the antigen bound to a substrate (e.g. an ELISA 96-well plate). Excess sera is thoroughly washed away. A labeled (enzyme-linked, fluorescent, radioactive, etc.) monoclonal antibody is then reacted with the previously reacted antigen-serum antibody complex. The amount of inhibition of monoclonal antibody binding is measured relative to a control (no patient serum antibody). The degree of monoclonal antibody inhibition is a very specific test for a particular variety or strain since it is based on monoclonal antibody binding specificity. MAbs can also be used for detection directly in cells by IFA.

Micro-Agglutination Assay

A micro-agglutination test can also be used to detect the presence of an *H. hepaticus* strain in a subject. Briefly, latex beads (or red blood cells) are coated with the antigen and mixed with a sample from the subject, such that antibodies in the tissue or body fluids that are specifically reactive with the antigen crosslink with the antigen, causing agglutination. The agglutinated antigen-antibody complexes form a precipitate, visible with the naked eye or by spectrophotometer. In a modification of the above test, antibodies specifically reactive with the antigen can be bound to the beads and antigen in the tissue or body fluid thereby detected.

Sandwich Assay/Flow Cytometry/Immunoprecipitation

In addition, as in a typical sandwich assay, the antibody can be bound to a substrate and reacted with the antigen. Thereafter, a secondary labeled antibody is bound to epitopes not recognized by the first antibody and the secondary antibody is detected. Since the present invention provides the *H. hepaticus* bacterium, other serological methods such as flow cytometry and immunoprecipitation can also be used as detection methods.

Nucleic acids

An isolated nucleic acid specific for *H. hepaticus* is also provided. An example of such a nucleic acid comprises the nucleotide sequence defined in the Sequence Listing as SEQ ID NO:1 is provided. This is a unique 16S ribosomal RNA fragment of *H. hepaticus*. An isolated double-stranded nucleic acid encoding the 16S rRNA is also specific for *H. hepaticus* and is also provided. Such a nucleic acid can be used for diagnosis of infection with *H. hepaticus*, for example, by polymerase chain reaction or sequence comparison.

An isolated nucleic acid that selectively hybridizes under stringent conditions with and has at least 85% sequence complementarity with the segment the strand of the of the 16S rDNA of *H. hepaticus* to which it hybridizes is also provided. As used herein to describe nucleic acids, the term "selectively hybridizes" means the same as "specific hybridization" and excludes the occasional randomly hybridizing nucleic acids as well as nucleic acids that encode ribosomal RNAs from other species. The selectively hybridizing nucleic acids can be used, for example, as probes or primers for detecting the presence of an organism that has the nucleic acid to which it hybridizes. Thus, the invention provides a method of detecting *H. hepaticus* infection in a subject, comprising detecting the presence of the selectively hybridizing nucleic acid in a specimen from the subject, the presence of the nucleic acid indicating infection with *H. hepaticus*.

The selectively hybridizing nucleic acids of the invention can have at least 70%, 80%, 85%, 90%, 95%, 97%, 98% and 99% complementarity with the segment and strand of the sequence to which it hybridizes. The nucleic acids are typically 12 to 4000 nucleotides in length. Thus, the nucleic acid can be used as a probe or primer for detecting the presence *H. hepaticus*. If used as primers, the invention provides compositions including at least two nucleic acids which selectively hybridize with different regions on the two strands of the DNA so as to amplify a desired region. For example, for the purpose of diagnosing the presence of *H. hepaticus*, the degree of complementarity between the hybridizing nucleic acid (probe or primer) and the sequence to which it hybridizes (*H. hepaticus* DNA from a sample) should be at least enough to exclude hybridization with a nucleic acid from a related bacterium (e.g. other Helicobacter species). Thus, a nucleic acid that selectively hybridizes with a *H. hepaticus* 16S rDNA sequence will not selectively hybridize under stringent conditions with a nucleic acid for a 16S rDNA of another species (*H. muridarum*, *H. pylori*, etc.), and vice versa. The degree of complementarity required to distinguish selectively hybridizing from nonselectively hybridizing nucleic acids under stringent conditions can be readily determined for each nucleic acid by testing it for its ability to hybridize under stringent conditions with non-*H. hepaticus* bacteria.

"Stringent conditions" refers to the washing conditions used in a hybridization protocol. In general, the washing conditions should be a combination of temperature and salt concentration chosen so that the denaturation temperature is approximately 5°–20° C. below the calculated $T_m$ (melting/denaturation temperature) of the hybrid under study. The temperature and salt conditions are readily determined empirically in preliminary experiments in which samples of reference DNA immobilized on filters are hybridized to the probe or coding nucleic acid of interest and then washed under conditions of different stringencies. For hybridization with a large oligonucleotide probe (e.g., 470 bp) hybridization is at 68° C. in the presence of 5× SSPE (49), followed by removing the non-specific hybrids by high-stringency washes of 0.1× SSPE at 68° C. as described in Sambrook et al. (49), chapter 9. Hybridizations with oligonucleotide probes of 18 or fewer nucleotides in length are done at 5°–10° C. below the estimated $T_m$ in 6× SSPE, then washed at the same temperature in 2× SSPE as described in Sambrook et al. (49), chapter 11. The $T_m$ of an oligonucleotide can be estimated by allowing 2° C. for each A or T nucleotide, and 4° C. for each G or C. An 18 nucleotide probe or primer of 50% G+C would, therefore, have an approximate $T_m$ of 54° C. Thus, stringent conditions for such an 18 nucleotide probe or primer would be a $T_m$ of about 54° C. and washing a salt concentration of about 0.1× SSPE, which can be modified as necessary in preliminary experiments.

It is noted that detection of the bacterium of the present invention can include consideration of characteristics other than the presence of the disclosed 16S ribosomal RNA or DNA sequence provided herein. By considering other characteristics, such as biochemical or ultrastructural features of an isolated bacterium, it is possible to determine the presence of *H. hepaticus* isolates that do not have the identical 16S rRNA sequence provided in SEQ ID NO:1. It is expected that the 16S cistron of such an isolate can selectively hybridize with the disclosed DNA since there will be sufficient sequence similarity between the newly obtained isolate and the type strain provided herein.

Vectors and Hosts

A nucleic acid of the present invention in a vector suitable for expression of the nucleic acid is also provided. The vector can be in a host suitable for expressing the nucleic acid.

There are numerous *E. coli* expression vectors known to one of ordinary skill in the art useful for the expression of the antigen. Other microbial hosts suitable for use include bacilli, such as *Bacillus subtilus*, and other enterobacteriaceae, such as Salmonella, Serratia, and various Pseudomonas species. Additionally, yeast expression can be used. Mammalian cells permit the expression of proteins in an environment that favors important post-translational modifications such as folding and cysteine pairing, addition of complex carbohydrate structures, and secretion of active protein.

Polynucleotides encoding a variant polypeptide may include sequences that facilitate transcription (expression sequences) and translation of the coding sequences such that the encoded polypeptide product is produced. Construction of such polynucleotides is well known in the art. For example, such polynucleotides can include a promoter, a transcription termination site (polyadenylation site in eukaryotic expression hosts), a ribosome binding site, and, optionally, an enhancer for use in eukaryotic expression hosts, and, optionally, sequences necessary for replication of a vector.

The DNA sequences can be expressed in hosts after the sequences have been operably linked to, i.e., positioned to ensure the functioning of, an expression control sequence. These expression vectors are typically replicable in the host organisms either as episomes or as an integral part of the host chromosomal DNA. Commonly, expression vectors can contain selection markers, e.g., tetracycline resistance or hygromycin resistance, to permit detection and/or selection of those cells transformed with the desired DNA sequences (see, e.g., U.S. Pat. No. 4,704,362).

Nucleic Acid Detection Methods

Having provided a nucleic acid specific for *H. hepaticus*, the invention provides a method of detecting the presence of *H. hepaticus* in a sample from a subject, comprising amplifying a DNA in the sample that is specific for *H. hepaticus* and detecting the presence of amplification, the presence of amplification indicating the presence of *H. hepaticus* in the sample.

As more specifically exemplified below, a nucleic acid sequence specific for *H. hepaticus* can comprise nucleic acids coding for 16S ribosomal RNA subunit. It is apparent that a skilled artisan can apply the methods described herein for detecting the 16S ribosomal RNA gene to detect other nucleic acid sequences specific for *H. hepaticus*. Examples of other sequences specific for *H. hepaticus* can include the genes for, urease, citrate synthase, heat shock protein, antigenic proteins and certain metabolic and synthetic enzymes. These genes can be obtained using probes based on the same gene from related species. The prospective *H. hepaticus* specific gene can then be amplified and sequenced according to methods known in the art. The specificity of these sequences for *H. hepaticus* can be determined by conducting a computerized comparison with known sequences, catalogued in GenBank, a computerized database, using the computer program Gap of the Genetics Computer Group (Madison Wisconsin) or other available nucleic acid sequence databases, which search the catalogued sequences for similarities to the gene in question.

The nucleic acid specific for the antigen can be detected utilizing a nucleic acid amplification technique, such as polymerase chain reaction or ligase chain reaction. PCR primers which hybridize only with nucleic acids specific for the antigen can be utilized. The presence of amplification indicates the presence of the organism. Thus, the present invention provides a method of detecting the presence of *H. hepaticus* by selective amplification. In yet another embodiment *H. hepaticus* can be detected by directly hybridizing the unique sequence with a specifically or selectively hybridizing nucleic acid probe. Furthermore, the nucleotide sequence could be amplified prior to hybridization by the methods described above.

Alternatively, the nucleic acid is detected utilizing direct hybridization or by utilizing a restriction fragment length polymorphism. For example, the present invention contemplates a method of detecting the presence of *H. hepaticus*, comprising ascertaining the presence of a nucleotide sequence associated with a restriction endonuclease cleavage site. In another embodiment a nucleic acid in a sample can be sequenced directly using, for example, Sanger ddNTp sequencing or 7-deaza-2'-deoxyguanosine 5'-triphosphate and compared to the corresponding sequence of other organisms.

Model for Chronic Helicobacter infection

A method of making an animal model for chronic Helicobacter infection is also provided. The method comprises administering to an animal an infectious amount of *H. hepaticus*, the resulting infected animal being a model for Helicobacter infection. The animal can, for example, be a mouse.

Among the diseases that can be modeled include chronic infections that lead to cancer. For example, chronic infection with certain strains of *H. pylori* is associated with the development of gastric carcinoma in humans. The *H. hepaticus* of the present invention is shown in the Examples to be associated with hepatocellular adenomas or carcinomas in certain strains of mice. Thus, a model of solid tumor formation is provided.

This model also permits the testing of anti-Helicobacter drugs. The model provides a bioassay for screening substances for the ability to inhibit the growth and or survival of Helicobacter species, comprising administering the substance to the animal infected with *H. hepaticus*, determining the survival or growth or the bacterium in the substance-treated animal and selecting those substances which inhibit the survival or growth of the bacterium in the animal. The model also provides a bioassay for screening substances for the ability to prevent or treat the toxic or carcinogenic action of Helicobacter species.

The following examples are intended to illustrate the invention. Various other examples and modifications of the foregoing description will be apparent to a person skilled in the art without departing from the spirit and scope of the invention, and it is intended that all such examples and modifications be included within the scope of the appended claims.

EXAMPLE 1

Chronic Active Hepatitis and Associated Liver Tumors In Mice Caused By A Novel Helicobacter Species The present findings document an important new infectious disease of mice which suggests a model for studies of chronic hepatic and gastric bacterial infection and cancer.

In the fall of 1992, a novel type of chronic, active hepatitis in mice was found in a large animal production and medical research facility. The mice were maintained in accordance with the Public Health Service Policy on Humane Care and Use of Laboratory Animals, revised 1986. They were free of common murine pathogens including mouse hepatitis virus.) This disease, defined by a distinctive morphologic pattern of liver damage has not been previously diagnosed in mice from any other location worldwide nor produced experimentally by injection of any known infectious agent.

Liver Disease

Liver disease was found in mice maintained in both production and research facilities. Rats, guinea pigs, and hamsters were not affected. Mice up to 12 months of age did not show signs of illness, except for ulcerative skin lesions in mice of one strain and the development of liver tumors in male mice in a long term (52–78 week) experiment. Reproductive performance was normal in mice from our breeding facilities. Some mouse strains were highly susceptible to the development of liver lesions (including A/JCr, C3H/HeNCr, BALB/cAnNCr, SCID/NCr) while others were highly resistant (C57BL/6NCr, B6C3F1, and nude (nu/nu) mice of various genetic backgrounds). Male mice were more severely affected than female mice. The disease could only be diagnosed at necropsy based on characteristic acute to chronic hepatic lesions identifiable in H&E stained tissue sections. To date, the chronic active hepatitis has been diagnosed in at least 15 strains of mice in 16 buildings located at the Frederick Cancer Center premises.

Some naturally-infected mice were euthanized at different ages (2–10 months of age) to study sequential histological changes in the liver. The earliest lesions seen, at 2–6 months of age, were focal necrosis and focal subacute nonsuppurative inflammation. Individual hepatocyte necrosis was also seen within these inflammatory lesions. By 6–10 months of age, additional chronic lesions developed including oval cell (bile ductule) hyperplasia extending from portal areas, portal lymphoplasmacytic infiltrates, postnecrotic fibrosis and cholangitis, hepatocytomegaly and intranuclear degenerative changes including inclusions of various types. Steiner's silver stain (3) was found to be especially effective in detecting organisms. Using this stain, helical-shaped bacteria were found within bile canaliculi adjacent to areas of necrosis and chronic inflammation. Ultrastructural examination of the liver lesions revealed bacteria only within bile canaliculi adjacent to lesions but not within areas of necrosis. Some mice also had focal chronic gastritis and typhlitis.

In one group of experimentally-infected male A/JCr mice a high incidence (100%) of hepatocellular adenomas or carcinomas were found by 78 weeks of age. All mice had chronic active hepatitis and most had helical bacteria evident with Steiner's stain. Two years previously (4), A/JCr male mice of the same age had less than a 5% incidence of hepatocellular neoplasms, prior to the finding of hepatitis in our barrier maintained mice. Few other groups of mice from susceptible strains were kept past one year of age in our production or research facilities.

Infection of mice with liver homogenates

Hepatitis was transmitted to young male A/J mice (from Jackson Laboratories) by intraperitoneal inoculation with approximately 10% liver homogenates from affected SCID/NCr mice. No clinical signs developed in these mice by 5 months but mice euthanized after 5.5, 10 and 18 weeks had liver lesions, including focal necrosis, focal nonsuppurative inflammation and oval cell hyperplasia. Helical organisms, similar to those seen in stained liver sections of natural infections, were noted with Steiner's stain.

Isolation and characterization of the disease causing agent

Livers from several male SCID/NCr mice with natural infections were removed aseptically and direct wet-mount impression smears of cut surfaces of tissue were examined under darkfield microscopy (1250×). Motile, helical organisms with a morphology similar to organisms seen in fixed and stained tissue sections were observed. Remaining liver tissues were spread over the surface of Columbia blood agar plates (Remel Labs, Lenexa, Kans.) and the plates were incubated at 37° C. under anaerobic conditions (Gaspak system, BBL Microbiology Systems, Cockeysville, Md.) or microaerophilic conditions. After one week of incubation, a thin, spreading film was seen over the agar surface. Darkfield examination of unstained material from the plate surfaces also confirmed the presence of large numbers of motile, helical organisms. Attempts to adapt organisms to a variety of broth media were unsuccessful. Helical organisms were maintained on blood agar plates by removal of a block of agar, inverting the agar block on a fresh blood agar plate, and pushing the block over the agar surface with an inoculating loop. Growth was not obtained when cultures were incubated at 25° C. or 42° C. under microaerophilic conditions.

The characteristics of the organism leading to classification as a Helicobacter species included production of enzymes present in other Helicobacter species including urease, catalase, and oxidase, resistance to nalidixic acid and cephalothin growth, under microaerophilic conditions, partial growth under anaerobic conditions, morphology and molecular biology. Scanning electron microscopy of the bacteria demonstrated two bipolar sheathed flagella and a smooth surface bacterial wall. Transmission electron microscopy showed a single polar flagellum but no evidence of periplasmic filament bundles.

PCR amplification and cycle sequencing

PCR amplification of 16S rRNA gene was performed using Ampliwax PCR Gem mediate "hot start" in a Perkin-Elmer Thermal Cycler 480 (Perkin-Elmer, Norwalk, Conn.). Reaction mixtures included 25 ng of sample DNA prepared as described in Example 2 (45) and 800 mg/ml of each primer. The primer set used for amplification included a forward primer (5'-AGAGTTYGATYCTGGCT-3' (SEQ ID NO:2); E. coli position 8 to 24) and a reverse primer (5'-TACGGYTACCTTGTTACGACT-3' (SEQ ID NO:3); E. coli position 1493 to 1513). Conditions for PCR amplification consisted of 25 cycles at 94° C. for 30 sec, 50° C. for 30 sec, and 70° C. for 60 sec with an increase of 3 sec at every cycle. The final cycle had a 50 min chain elongation at 72° C. Amplified PCR products were separated on 1% agarose gels to determine whether correctly-sized products (approximately 1500 base pairs) were obtained. The direct PCR products were combined and then precipitated with polyethylene glycol 2000 (45). The primers used for cycle sequencing are as described above and in Example 2 (45). A forward primer (5'-GGAATCGCTAGTAATCG-3' (SEQ ID NO:4); E. coli position 1337 to 1353) instead of the reverse primer described above was used to sequence the 3' end. The primers were labeled with 33P-ATP and conditions for cycle sequencing were as described by the manufacturer (USB, Cleveland, Ohio).

PCR amplification and sequencing of 16S RRNA from the bacteria (5) revealed that this organism is a new species of Helicobacter. Phylogenetic analysis of the new Helicobacter species (further described in Example 2) revealed the closest degree of sequence identity to H. muridarum (~98%). Phenotypic, biochemical and molecular characterization of the new species of Helicobacter are provide in Example 2.

Infection of mice with cultured organism

A concentrated suspension from a pure culture of the new Helicobacter organism was injected ip (intraperitoneally) or intragastrically into 4 week old male A/J mice. By 4–7 weeks, focal necrosis and inflammation was seen in the livers of the injected mice and organisms were demonstrated by Steiner's stain. Bacteria were re-isolated on blood agar from these livers. These organisms had the same characteristics as the isolates made initially from naturally affected livers. The hepatitis has also been successfully reproduced in germ-free mice by oral inoculation of H. hepaticus.

Immunoblot with sera from infected mice

Sera obtained from mice that were naturally or experimentally infected with Helicobacter sp were analyzed by immunoblot techniques (6). Briefly, mouse Helicobacter cultures were disrupted with SDS, heated to 95° C., separated by sodium dodecyl sulfate-polyacrylamide gel electrophoresis (SDS-PAGE) through a 10 to 20% gradient gel and transferred to Immobilon paper (Millipore Corp., Bedford, Pa.) by electrophoresis (6). Strips were incubated with mouse sera (1:50 dilution), and the presence of antigen-antibody complexes detected by incubation with peroxidase-conjugated anti-mouse IgG antiserum and development with chloronaphthol as described (6). Each strip contained approximately 7 mg of bacterial protein.

Sera from two A/J mice inoculated intraperitoneally contained readily detectable antibodies that cross-reacted with various proteins of approximately 50 to 90 kDa, as well as with a protein of 27 kDa. A similar pattern of antibody cross-reactivity was detected in naturally infected SJL/NCr mice, but not in uninfected BALB/c mice or A/J mice. Polypeptides with molecular masses of 50 kDa have been shown to be the most specific for the diagnosis of Helicobacter pylori infections in man (7). Further serological screening studies will assist in the identification of infected animals in mouse colonies, as well as determining the degree of serological cross-reactivity with other Helicobacter organisms.

Model for chronic Helicobacter infection

This chronic, active bacterial infection of the liver and GI tract appears to represent an excellent model for chronic Helicobacter infections. In particular, the high incidence of liver tumors in aging affected mice, and gastritis in some mice, can serve as an excellent model for studying the carcinogenic potential of this group of bacteria since H. pylori is associated with human gastric cancer (1).

With the ability to isolate and characterize this new murine pathogen (H. hepaticus), the extent of its presence in other mice colonies as well as its pathogenic potential can be determined. Furthermore, the present data and methods permit the identification of organisms of this species that can colonize other hosts including humans, and elicit a pathologic response.

EXAMPLE 2

Biochemical and Genetic Analysis of Helicobacter hepaticus

Isolation, morphology and Growth Characteristics of *H. hepaticus* strains.

Fifteen strains (Hh-1 through Hh-15), of *H. hepaticus* were isolated from the livers of SCID/NCr mice. In addition, 7 strains of *H. hepaticus* (Hh-16 through Hh-22) were isolated from either colonic or cecal mucosal scrapings from SCID/NCr or A/JCr mice. Briefly, the original isolate Hh-1, was isolated from liver of a mouse with multifocal hepatitis by streaking liver tissue and onto moist Columbia blood agar plates (Remel Labs, Lenexa Kans.) and incubating at 37° C. under anaerobic conditions (Gaspak System, BBL Microbiology Systems, Cockeysville, Md.). Subsequent isolations of bacteria from infected livers were performed on either moist TSA blood agar plates or brucella blood agar with TVP (trimethoprim, vancomycin, polymyxin) (Remel Labs, Lenexa Kans.) at 37° C. under microaerophilic conditions in vented jars containing $N_2$, $H_2$, and $CO_2$ (90:5:5:).

After a 3 to 7 day incubation under anaerobic or microaerophilic conditions, a thin spreading film was noted on the agar surface. Examination with phase microscopy revealed the presence of spiral shaped, motile bacteria. While the bacteria grow anaerobically, microaerophilic conditions were routinely used to isolate bacteria from the liver and are considered the optimal environmental conditions for growth of *H. hepaticus*. The bacteria were Gram negative, curved to spiral in shape and measured 1.5–5.0 µm long and 0.2–0.3 µm wide.

Electron microscopy and ultrastructure.

Cells grown on TSA blood agar plates were gently suspended in 10 mM Tris buffer (pH 7.4) at a concentration of approximately $10^8$ cells per ml. Samples were negatively stained with 1% (wt/vol) phosphotungstic acid (pH 6.5) for 15 to 20 seconds. Specimens were examined with a JEOL model JEM-1200EX transmission electron microscope operating at 100 kV.

The organism had a smooth surface and lacked periplasmic fibers, which are found in the 2 mouse intestinal Helicobacter species, "*H. rappini*" and *H. muridarum* (1,14). The organism varied in shape and size from curved to spiral with one to several spirals. The bacteria were characterized by single bipolar sheathed flagella.

Biochemical and physiological characteristics.

Detailed biochemical characterization was performed on strains Hh-1 through Hh-3 (Table 2) as previously described (1,37). In the remaining 19 strains, motility, Gram stain reaction, oxidase, catalase, and urease activities, and sensitivity to nalidixic acid and cephalothin were determined.

Three strains of *H. hepaticus* were subjected to a number of tests to distinguish biochemical and physiological properties which were then compared to known helicobacter species (Table 4). Like *H. muridarum* and "*H. rappini*", *H. hepaticus* has strong urease activity and was oxidase and catalase positive. *H. hepaticus* strains also produced $H_S$ using lead acetate, and reduced nitrate to nitrite. The bacteria grew microaerophically at 37° C., but not 25° C. or 42° C. The bacteria also grew in 1.5% NaCl, 1% glycine and 0.1% TMAO (anaerobically). *H. hepaticus* can be differentiated from the two other Helicobacter species of mice by ultrastructural morphology and biochemically by the ability of *H. hepaticus* to reduce nitrate and grow in 1% glycine. *H. hepaticus* did not hydrolyze hippurate, nor did it produce hemolysis in blood agar or produce yellow pigment. The remaining 19 strains were also Gram negative, curved to spiral in shape, motile, as well as catalase, oxidase, and strongly urease positive. All of the strains were resistant to both cephalothin and nalidixic acid but sensitive to metronidazole.

Like other Helicobacter species its normal ecological niche is probably the gastrointestinal tract. *H. hepaticus* is actively motile due to the single sheathed flagella at one or both ends of the bacteria. Like the two other intestinal colonizers of mice, *H. muridarum*, and "*H. rappini*", the presence of the flagella is probably important in colonization of mucus in the intestinal crypts. Different strains of *H. hepaticus* may exist with varying degrees of pathogenic potential. There is precedence for Helicobacter species causing hepatitis under certain circumstances: "*H. rappini*" can cross the placenta of pregnant sheep, induce abortions, and cause acute hepatic necrosis in sheep fetuses (14,27). Thus, *H. hepaticus* is similar to all other known helicobacter species in being an efficient colonizer of the gastrointestinal tract but in addition it has the pathogenic potential of being able to elicit hepatitis in several strains of mice and in one strain, the A/JCr, is strongly associated with hepatic cancer.

Crude DNA isolation.

Bacteria were cultured on TSA blood agar plates. A loopful of cells was harvested and suspended in 100 µl of lysis buffer (50 mM Tris-HCl, pH 7.6, 1 mM EDTA, 0.5% Tween 20, 200 µg/ml proteinase K) and incubated at 55° C. for 2 hrs. The proteinase K was inactivated by heating to 95° C. for 10 min. Crude DNA was then precipitated with 2 volumes of cold absolute ethanol.

Amplification of 16S rRNA cistrons.

The 16S rRNA cistrons were amplified using primers 1 & 2 in Table 1. PCR reactions were performed in thin-walled tubes using a Perkin-Elmer 480 thermal cycler. Ten µl of the crude DNA and 1 µM primers were added to the reaction mixture which had a final volume of 82 µl Ampliwax PCR Gem100's (Perkin-Elmer) were used in a hot-start protocol as suggested by the manufacturer. The following conditions were used for amplification; denaturation at 94° C. for 45 seconds, annealing at 50° C. for 45 seconds, and elongation at 72° C. for 45 seconds with 5 additional seconds added for each cycle. A total of 25 cycles were performed followed by a final elongation step at 72° C. for 15 minutes. The purity of the amplified product was determined by electrophoresis in a 1% Agarose gel (FMC Bioproducts). DNA was stained with ethidium bromide and viewed under short wavelength UV light.

Purification of PCR products.

The amplified DNA was purified by precipitation with PEG 8000 (30). After removal of Ampliwax, 0.6 volumes of 20% PEG 8000 (Sigma) in 2.5 M NaCl were added and the mixture incubated at 37° C. for 10 minutes. The sample was centrifuged for 15 minutes at 15,000×g and the pellet was washed with 80% ethanol and pelleted as before. The pellet was air dried and dissolved in 30 µl of distilled water and used for cycle sequencing as described below.

Sequencing.

The DNA sample from PCR was directly sequenced using a cycle-sequencing kit (TAQuence Cycle Sequencing Kit, United States Biochemical Corp). The manufacturers protocol was followed. The six sequencing primers are given in Table 1. Primers were end-labeled with $^{33}P$ (NEN/Dupont) using the manufacturers' protocol. Approximately 100 ng of purified DNA from the PCR was used for sequencing. Reaction products were loaded onto 8% polyacrylamide/urea gels, electrophoresed, and detected by exposure to X-ray film for 24 hours.

16S rRNA data analysis.

A program set for data entry, editing, sequence alignment, secondary structure comparison, similarity matrix generation, and dendrogram construction for 16S rRNA data was written in Microsoft QuickBASIC for use on IBM PC-AT and compatible computers (36). RNA sequences were entered and aligned as previously described (36). Our sequence database contains approximately 300 sequences determined in our laboratory, and another 200 obtained from Genbank or the Ribosomal Database Project (34). Reference strains used in the 16S rRNA analysis are given in Table 2. Similarity matrices were constructed from the aligned sequences by using only those sequence positions for which 90% of the strains had data. The similarity matrices were corrected for multiple base changes at single positions by the method of Jukes and Cantor (26). Phylogenetic trees were constructed using the Neighbor-Joining method of Saitou and Nei (40,43).

Phylogenetic Analysis.

We analyzed approximately 95% of the total RNA sequence for strains Hh-1, Hh-2, and Hh-3. The sequences for the 3 mouse liver strains were identical. Comparison of the consensus sequence with other bacteria in our database indicated that the *H. hepaticus* sequence was most closely related to that of *Helicobacter muridarum*, (97.8% similarity). This degree of sequence difference clearly identifies *H. hepaticus* as a novel species. Strain Hh-2 was compared with 26 reference species in the genera Helicobacter, Wolinella, Arcobacter, and Campylobacter. The similarity matrix for these comparisons is presented in Table 3. *H. hepaticus* falls in a cluster of intestinal Helicobacter species which includes *H. muridarum, H. canis, "H. rappini"* and *H. cinaedi*.

The phenotypic characteristics which differentiate *H. hepaticus* from other named and described species of Helicobacter are presented in Table 4.

Genbank accession numbers.

The Genbank and culture collection accession numbers for the strains examined in this report are given in Table 2.

Description of *Helicobacter hepaticus* sp. nov.

*Helicobacter hepaticus* (he.pat.i.cus G. hepatikos. Relating to the liver). Cells are curved to spiral slender rods (0.2–0.3 μm by 1.5–5.0 μm) which form one to three spiral turns. Gram negative. Nonsporulating. Motile by means of sheathed bipolar flagella, one at each end. Colonies are pinpoint, but cultures often appear as thin spreading layer on agar media. Microaerophilic or anaerobic growth, but no growth aerobically. Growth at 37° C., but not 25° C. or 42° C.; growth in 1.5% NaCl, 1% glycine, 0.4% TTC, and 0.1% TMAO (anaerobically). Produces urease, catalase, and oxidase activity. Nitrate is reduced. $H_S$ is detected on lead acetate discs. Hippurate is not hydrolyzed. Resistant to cephalothin and nalidixic acid, but sensitive to metronidazole. Isolated from colon and cecum of mice, and the livers of mice with active, chronic hepatitis. The type strain Hh-2 was isolated from the liver of a mouse with active chronic hepatitis. The type strain and other isolates were deposited on Apr. 21, 1994 with the American Type Culture Collection (12301 Parklawn Drive, Rockville, Md. 20852) as ATCC 51448. The essentially complete 16S rRNA sequence of the type strain (SEQ ID NO:1) is available for electronic retrieval from GenBank, EMBL and DDBJ databases under accession number U07574.

TABLE 1

Oligonucleotide primers used for PCR amplification and sequencing of 16S rDNA.

| Type | Sequence (5'-3')[a] | Position[b] | Orientation |
| --- | --- | --- | --- |
| PCR | AGAGTTGATYCTGGCT (SEQ ID NO: 2) | 8–24 | Forward |
| PCR | TACGGYTACCTTGTTACGACT (SEQ ID NO: 3) | 1493–1513 | Reverse |
| Sequencing | ACTGCTGCCTCCCGT (SEQ ID NO: 5) | 344–358 | Reverse |
| Sequencing | GTRTTACCGCGGCTGCTG (SEQ ID NO: 6) | 519–536 | Reverse |
| Sequencing | CTACCAGGGTATCTAATC (SEQ ID NO: 7) | 786–804 | Reverse |
| Sequencing | GGTTGCGCTCGTTGCGGG (SEQ ID NO: 8) | 1096–1113 | Reverse |
| Sequencing | GGAATCGCTAGTAATCG (SEQ ID NO: 4) | 1337–1353 | Forward |
| Sequencing | CCCGGGAACGTATTCACCG (SEQ ID NO: 9) | 1369–1387 | Reverse |

[a]Base codes are standard Internation Union of Biochemistry codes for bases and ambiguity.
[b]Numbering based upon *E. coli*.

TABLE 2

Sources and accession numbers of strains studied

| Organism | Strain examined[a] | Culture Collections[b] | GenBank[c] accession no. |
| --- | --- | --- | --- |
| Isolates | | | |
| *H. hepaticus* | Fox Hh-1 | ATCC 51449 | U07573 |

TABLE 2-continued

Sources and accession numbers of strains studied

| Organism | Strain examined[a] | Culture Collections[b] | GenBank[c] accession no. |
|---|---|---|---|
| H. hepaticus | Fox Hh-2 ™ | ATCC 51448 ™ | U07574 |
| H. hepaticus | Fox Hh-3 | ATCC 51450 | U07575 |
| Reference species | | | |
| A. cryophilus | CCUG 17801 ™ | ATCC 43158 ™ | L14624 |
| A. butzleri | CCUG 10373 | | L14626 |
| A. skirrowii | CCUG 10374 ™ | | L16625 |
| C. coli | CCUG 11238 ™ | ATCC 33559 ™ | L04312 |
| C. concisus | Tanner 484 ™ | ATCC 33237 ™ | L04322 |
| C. fetus ss fetus | ATCC 27374 ™ | | M65012 |
| C. lari | CCUG 23947 ™ | ATCC 35221 ™ | L04316 |
| C. rectus | Tanner 371 ™ | ATCC 33238 ™ | L04317 |
| "F. rappini" | NADC 1893 ™ | ATCC 43966 ™ | M88137 |
| "Gastrospirillum hominis 1" | | | L10079 |
| "Gastrospirillum hominis 2" | | | L10080 |
| H. acinonyx | Eaton 90-119-3 ™ | ATCC 51101 ™ CCUG 29263T ™ | M88148 |
| H. canis | NCTC 12739 ™ | | L13464 |
| H. cinaedi | CCUG 18818 ™ | ATCC 35683 ™ | M88150 |
| H. felis | Lee CS1 ™ | ATCC 49179 ™ | M37642 |
| H. fennelliae | CCUG 18820 ™ | ATCC 35684 ™ | M88154 |
| H. mustelae | Fox R85-13-6 ™ | ATCC 43772 ™ | M35048 |
| H. muridarum | Lee ST1 ™ | CCUG 29262 ™ ATCC 49282 ™ | M80205 |
| H. nemestrinae | — | ATCC 49396 ™ | X67854 |
| H. pametensis | Seymour B9 ™ | CCUG 29255 ™ | M88147 |
| H. pylori | ATCC 43504 ™ | | M88157 |
| Helicobacter sp. "CLO-3" (human) | CCUG 14564 | LMG 7792 | M88151 |
| Helicobacter sp. "B" (bird) | Seymour B10 ™ | CCUG 29256 ™ | M88139 |
| Helicobacter sp. "C" (bird) | Seymour B52 ™ | CCUG 29561 ™ | M88144 |
| W. succinogenes | Tanner 602W ™ | ATCC 29543 ™ | M88159 |

[a]Stains from which sequences were determined were obtained from the following individuals or culture collections: K. A. Eaton, Department of Veterinary Pathobiology, Ohio State University, Columbus, Ohio; J. G. Fox, Division of Comparative Medicine, Massachusetts Institute of Technology, Cambridge, Mass.; A. Lee, Department of Microbiology and Immunology, University of New South Wales, Sydney; C. Seymour, Department of Microbiology, Boston University School of Medicine, Boston, Mass.; A. Tanner, Department of Microbiology, Forsyth Dental Center, Boston, Mass; ATCC, American Type Culture Collection, Rockville, Maryland; CCUG, Culture Collection, University of Göeteborg, Göeteborg, Sewden; LMG, Laboratorium voor Microbiologie en microbielle Genetica, Ghent, Belgium; NADC, National Animal Disease Center, Ames, Iowa; or NCTC, National Collections of Type Cultures, London, United Kingdom.
[b]Aternate culture collection sources for sequenced strains. Abrevations as above.
[c]16S rRNA sequences for these strains are available for electronic retrieval from GenBank under the following accession numbers. Through cross distribution of data bases, these sequences should also be available from EMBL and DDBJ.

TABLE 3

Similarity matrix based upon 16S rRNA sequence comparisons[a]

| | H.he | H.mr | H.ca | F.ra | H.ci | H.fe | H.s3 | H.py | H.ne | H.ac | G.h1 | G.h2 | H.fe |
|---|---|---|---|---|---|---|---|---|---|---|---|---|---|
| *Helicobacter hepaticus* | . | 97.8 | 97.3 | 97.4 | 97.0 | 95.5 | 95.2 | 93.5 | 93.6 | 93.2 | 92.3 | 92.8 | 93.3 |
| *Helicobacter muridarum* | 2.3 | . | 96.5 | 96.1 | 95.9 | 95.1 | 94.3 | 93.1 | 93.1 | 92.5 | 91.9 | 92.4 | 92.6 |
| *Helicobacter canis* | 2.8 | 3.6 | . | 98.0 | 97.8 | 95.4 | 96.0 | 93.9 | 93.8 | 93.2 | 92.3 | 92.7 | 93.2 |
| "*Flexispira rappini*" | 2.6 | 4.0 | 2.0 | . | 98.8 | 95.4 | 95.5 | 93.2 | 93.4 | 92.5 | 92.2 | 92.3 | 92.6 |
| *Helicobacter cinaedi* | 3.1 | 4.2 | 2.3 | 1.2 | . | 95.9 | 95.3 | 92.8 | 93.3 | 92.4 | 92.0 | 92.4 | 92.6 |
| *Helicobacter fennelliae* | 4.6 | 5.1 | 4.7 | 4.8 | 4.3 | . | 94.8 | 93.1 | 92.8 | 92.3 | 92.6 | 92.8 | 93.0 |
| Helicobacter sp. "CLO-3" | 4.9 | 5.9 | 4.1 | 4.6 | 4.9 | 5.4 | . | 93.9 | 93.4 | 93.0 | 92.7 | 92.8 | 93.2 |
| *Helicobacter pylori* | 6.8 | 7.2 | 6.4 | 7.1 | 7.5 | 7.3 | 6.4 | . | 98.2 | 97.4 | 94.9 | 95.1 | 95.4 |
| *Helicobacter nemestrinae* | 6.7 | 7.3 | 6.4 | 6.9 | 7.0 | 7.6 | 6.9 | 1.8 | . | 96.7 | 94.7 | 94.9 | 95.5 |
| *Helicobacter acinonyx* | 7.1 | 8.0 | 7.1 | 7.9 | 8.0 | 8.1 | 7.4 | 2.6 | 3.3 | . | 94.7 | 96.0 | 96.4 |
| "*Gastrospirillum hominis*" 1 | 8.1 | 8.6 | 8.1 | 8.3 | 8.4 | 7.8 | 7.6 | 5.3 | 5.5 | 5.5 | . | 96.5 | 96.6 |
| "*Gastrospirillum hominis*" 2 | 7.6 | 8.0 | 7.6 | 8.1 | 8.0 | 7.6 | 7.5 | 5.1 | 5.3 | 4.1 | 3.6 | . | 98.8 |
| *Helicobacter felis* | 7.0 | 7.8 | 7.1 | 7.7 | 7.8 | 7.3 | 7.1 | 4.7 | 4.7 | 3.7 | 3.4 | 1.3 | . |
| *Helicobacter pametensis* | 3.8 | 4.5 | 3.6 | 3.6 | 4.6 | 4.6 | 5.0 | 5.7 | 5.6 | 6.3 | 7.8 | 6.6 | 6.3 |
| Helicobacter sp. "C" (bird) | 3.6 | 3.8 | 3.2 | 3.7 | 4.5 | 5.6 | 4.7 | 6.1 | 5.7 | 6.8 | 8.2 | 7.5 | 7.1 |
| Helicobacter sp. "B" (bird) | 3.6 | 4.1 | 3.2 | 4.3 | 4.8 | 5.6 | 5.0 | 6.5 | 6.2 | 6.8 | 8.2 | 7.3 | 6.9 |
| *Helicobacter mustelae* | 3.7 | 4.4 | 3.7 | 4.3 | 5.0 | 5.8 | 4.9 | 6.4 | 6.2 | 6.8 | 8.4 | 7.1 | 6.9 |
| *Wolinella succinogenes* | 7.6 | 6.9 | 6.9 | 7.3 | 7.4 | 7.9 | 8.0 | 9.8 | 9.5 | 10.1 | 11.5 | 10.7 | 10.5 |
| *Arcobacter cryaerophilus* | 16.8 | 16.8 | 16.2 | 16.7 | 16.7 | 17.4 | 16.1 | 17.4 | 16.8 | 17.7 | 18.7 | 18.4 | 18.7 |
| *Arcobacter skirrowii* | 17.3 | 17.2 | 16.7 | 17.2 | 17.3 | 17.6 | 16.6 | 18.0 | 17.5 | 18.1 | 19.1 | 19.0 | 18.9 |
| *Arcobacter butzleri* | 15.8 | 15.7 | 15.6 | 16.1 | 16.2 | 16.0 | 15.1 | 16.3 | 16.0 | 16.6 | 18.3 | 17.9 | 17.7 |
| *Campylobacter rectus* | 16.2 | 17.0 | 16.0 | 15.6 | 15.8 | 16.2 | 16.5 | 17.8 | 17.0 | 18.5 | 19.1 | 19.4 | 19.3 |

TABLE 3-continued

Similarity matrix based upon 16S rRNA sequence comparisons[a]

| | | | | | | | | | | | | | |
|---|---|---|---|---|---|---|---|---|---|---|---|---|---|
| Campylobacter concisus | 14.2 | 15.1 | 14.0 | 13.8 | 14.0 | 14.3 | 14.6 | 16.6 | 15.5 | 17.0 | 17.2 | 17.4 | 17.3 |
| Campylobacter fetus | 15.3 | 16.0 | 14.9 | 14.6 | 15.0 | 15.4 | 15.6 | 16.6 | 15.9 | 17.3 | 17.4 | 17.4 | 17.4 |
| Campylobacter helveticus | 14.8 | 15.0 | 14.0 | 14.1 | 15.1 | 15.5 | 15.6 | 16.0 | 15.3 | 16.5 | 16.7 | 16.7 | 16.7 |
| Campylobacter lari | 14.7 | 15.2 | 14.1 | 14.1 | 14.8 | 14.6 | 14.8 | 16.0 | 15.5 | 16.4 | 16.8 | 16.7 | 16.6 |
| Campylobacter jejuni | 15.4 | 15.8 | 14.7 | 14.7 | 15.5 | 15.2 | 15.7 | 16.2 | 15.8 | 16.7 | 17.5 | 17.2 | 17.2 |

| | H.pa | H.sC | H.sB | H.ms | W.su | A.cr | A.sk | A.bu | C.re | C.co | C.fe | C.he | C.la | C.je |
|---|---|---|---|---|---|---|---|---|---|---|---|---|---|---|
| Helicobacter hepaticus | 96.3 | 96.5 | 96.5 | 96.4 | 92.8 | 84.9 | 84.6 | 85.8 | 85.5 | 87.1 | 86.1 | 86.6 | 86.6 | 86.1 |
| Helicobacter muridarum | 95.7 | 96.3 | 96.0 | 95.8 | 93.4 | 85.0 | 84.6 | 85.8 | 84.8 | 86.4 | 85.6 | 86.4 | 86.2 | 85.8 |
| Helicobacter canis | 96.5 | 96.9 | 96.8 | 96.4 | 93.4 | 85.4 | 85.0 | 85.9 | 85.6 | 87.2 | 86.5 | 87.2 | 87.1 | 86.6 |
| "Flexispira rappini" | 96.5 | 96.4 | 95.8 | 95.8 | 93.1 | 85.1 | 84.7 | 85.5 | 85.9 | 87.4 | 86.7 | 87.1 | 87.2 | 86.7 |
| Helicobacter cinaedi | 95.5 | 95.6 | 95.4 | 95.2 | 92.9 | 85.0 | 84.6 | 85.4 | 85.8 | 87.2 | 86.4 | 86.3 | 86.5 | 86.0 |
| Helicobacter fennelliae | 95.5 | 94.6 | 94.6 | 94.4 | 92.5 | 84.5 | 84.3 | 85.6 | 85.4 | 87.0 | 86.1 | 86.0 | 86.8 | 86.2 |
| Helicobacter sp. "CLO-3" | 95.1 | 95.5 | 95.2 | 95.2 | 92.4 | 85.5 | 85.1 | 86.3 | 85.2 | 86.8 | 85.9 | 85.9 | 86.6 | 85.9 |
| Helicobacter pylori | 94.5 | 94.2 | 93.8 | 93.9 | 90.9 | 84.5 | 84.0 | 85.3 | 84.1 | 85.1 | 85.1 | 85.6 | 85.6 | 85.4 |
| Helicobacter nemestrinae | 94.6 | 94.5 | 94.0 | 94.0 | 91.0 | 85.0 | 84.4 | 85.6 | 84.8 | 86.0 | 85.7 | 86.2 | 86.0 | 85.7 |
| Helicobacter acinonyx | 94.0 | 93.5 | 93.5 | 93.5 | 90.6 | 84.2 | 83.9 | 85.1 | 83.6 | 84.8 | 84.6 | 85.2 | 85.2 | 85.0 |
| "Gastrospirillum hominis" 1 | 92.6 | 92.2 | 92.2 | 92.0 | 89.3 | 83.5 | 83.2 | 83.7 | 83.2 | 84.6 | 84.5 | 85.0 | 84.9 | 84.4 |
| "Gastrospirillum hominis" 2 | 93.7 | 92.9 | 93.0 | 93.2 | 90.0 | 83.7 | 83.2 | 84.1 | 82.9 | 84.5 | 84.4 | 85.0 | 85.1 | 84.6 |
| Helicobacter felis | 93.9 | 93.2 | 93.4 | 93.4 | 90.2 | 83.5 | 83.3 | 84.2 | 83.0 | 84.5 | 84.5 | 85.0 | 85.1 | 84.6 |
| Helicobacter pametensis | . | 98.1 | 97.9 | 97.2 | 94.2 | 86.0 | 85.6 | 86.5 | 85.9 | 87.6 | 86.5 | 87.2 | 87.7 | 87.2 |
| Helicobacter sp. "C" (bird) | 2.0 | . | 98.3 | 98.0 | 94.6 | 85.6 | 85.1 | 86.3 | 85.5 | 86.8 | 86.6 | 87.3 | 87.7 | 87.1 |
| Helicobacter sp. "B" (bird) | 2.1 | 1.8 | . | 98.7 | 94.2 | 86.1 | 85.9 | 86.9 | 85.1 | 86.5 | 86.2 | 86.9 | 87.2 | 86.9 |
| Helicobacter mustelae | 2.9 | 2.1 | 1.3 | . | 93.8 | 86.0 | 85.6 | 86.5 | 84.8 | 86.1 | 85.8 | 86.5 | 87.2 | 86.6 |
| Wolinella succinogenes | 6.1 | 5.6 | 6.1 | 6.4 | . | 85.6 | 85.2 | 86.1 | 86.3 | 86.3 | 85.9 | 86.0 | 86.8 | 86.4 |
| Arcobacter cryaerophilus | 15.4 | 16.0 | 15.3 | 15.4 | 15.9 | . | 99.0 | 97.4 | 86.1 | 87.6 | 86.1 | 86.5 | 87.2 | 87.3 |
| Arcobacter skirrowii | 16.0 | 16.6 | 15.6 | 16.0 | 16.4 | 1.0 | . | 97.3 | 85.6 | 87.6 | 86.0 | 86.2 | 86.9 | 87.2 |
| Arcobacter butzleri | 14.9 | 15.2 | 14.4 | 14.9 | 15.3 | 2.6 | 2.8 | . | 86.6 | 88.0 | 86.1 | 86.4 | 86.7 | 86.9 |
| Campylobacter rectus | 15.6 | 16.1 | 16.6 | 16.9 | 15.1 | 15.4 | 16.0 | 14.8 | . | 96.0 | 94.0 | 91.8 | 92.5 | 92.9 |
| Campylobacter concisus | 13.6 | 14.5 | 14.9 | 15.4 | 15.1 | 13.6 | 13.6 | 13.1 | 4.1 | . | 95.6 | 92.3 | 93.9 | 93.8 |
| Campylobacter fetus | 14.9 | 14.7 | 15.3 | 15.7 | 15.6 | 15.4 | 15.5 | 15.3 | 6.2 | 4.6 | . | 93.3 | 94.2 | 94.5 |
| Campylobacter helveticus | 14.0 | 13.9 | 14.4 | 14.9 | 15.5 | 14.9 | 15.3 | 15.0 | 8.6 | 8.1 | 7.0 | . | 96.7 | 97.1 |
| Campylobacter lari | 13.4 | 13.5 | 14.0 | 14.1 | 14.5 | 14.0 | 14.4 | 14.7 | 7.9 | 6.4 | 6.0 | 3.4 | . | 98.7 |
| Campylobacter jejuni | 14.0 | 14.1 | 14.4 | 14.7 | 15.1 | 13.9 | 14.1 | 14.4 | 7.5 | 6.5 | 5.7 | 3.0 | 1.3 | . |

[1]Numbers above the diagonal represent uncorrected percedntages of similarity and those below the diagonal are percentages of difference corrected for multiple base changes by the method of Jukes and Cantor.

TABLE 4

Characteristic which differentiate H. hepaticus from other Helicobacter species.[a]

| Taxon | Catalase production | Nitrate reduction | Alkaline phosphatase hydrolysis | Urease | Gamma-glutarnyl trans-peptidase | Indoxyl acetate hydroxysis | Growth at 42° C. |
|---|---|---|---|---|---|---|---|
| H. hepaticus | + | + | nd | + | nd | nd | − |
| H. muridarum | + | − | + | + | + | + | − |
| H. canis | − | − | + | − | nd | + | + |
| "Flexispira rappini" | + | − | − | + | + | nd | + |
| H. cinaedi | + | + | − | − | − | − | − |
| H. fennelliae | + | − | + | − | − | + | − |
| Helicobacter sp. "CLO-3" | + | − | + | − | − | + | + |
| H. pylori | + | − | + | + | + | − | − |
| H. nemestrinae | + | − | + | + | nd | − | + |
| H. acinonyx | + | − | + | + | + | − | − |
| H. felis | + | + | + | + | + | − | + |
| H. pametensis | + | + | + | − | − | − | + |
| Helicobacter sp. "C" (bird) | + | + | + | + | − | + | + |
| Helicobacter sp. "B" (bird) | + | + | + | + | − | + | + |
| H. mustelae | + | + | + | + | + | + | + |

| Taxon | Growth on 1% Glycine | Susceptibility Nalidixic acid 30 μg disc | Susceptibility Cepha-lothin 30 μg disc | Periplasmic fibers | Flagella number | Flagella distribution | G + C content (mole %) |
|---|---|---|---|---|---|---|---|
| H. hepaticus | + | R | R | − | 2 | Bipolar | nd |
| H. muridarum | − | R | R | + | 10–14 | Bipolar | 34 |
| H. canis | nd | S | I | − | 2 | Bipolar | 48 |
| "Flexispira rappini" | − | R | R | + | 10–20 | Bipolar | 34 |
| H. cinaedi | + | S | I | − | 1–2 | Bipolar | 37–38 |
| H. fennelliae | + | S | S | − | 2 | Bipolar | 35 |
| Helicobacter sp. "CLO-3" | + | I | R | − | | | 45 |

TABLE 4-continued

Characteristic which differentiate *H. hepaticus* from other Helicobacter species.[a]

| | | | | | | | |
|---|---|---|---|---|---|---|---|
| *H. pylori* | − | R | S | − | 4–8 | Bipolar | 35–37 |
| *H. nemestrinae* | − | R | S | − | 4–8 | Bipolar | 24 |
| *H. acinonyx* | − | R | S | − | 2–5 | Bipolar | 30 |
| *H. felis* | − | R | S | + | 14–20 | Bipolar | 42 |
| *H. pametensis* | + | S | S | − | 2 | Bipolar | 38 |
| Helicobacter sp. "C" (bird) | + | S | R | − | 2 | Bipolar | 30 |
| Helicobacter sp. "B" (bird) | + | S | R | − | 2 | Bipolar | 31 |
| *H. mustelae* | − | S | R | − | 4–8 | Peritrichous | 36 |

[a]Data were obtained from references (16, 42) and this study.
+, positive reaction;
−, negative reaction;
S, susceptible;
R, resistant;
I, intermediate;
nd, not determined.

Throughout this application various publications are referenced by numbers within parentheses. Full citations for these publications follow. The disclosures of these publications in their entireties are hereby incorporated by reference into this application in order to more fully describe the state of the art to which this invention pertains.

REFERENCES

1. M. J. Blaser, Clin. Inf. Dis. 15, 386 (1992.); Lee, et al., Inf. Imm. 61, 1601 (1993);J. G. Fox, B. M. Edrise, E. B. Cabot, C. Beaucage, and J. C. Murphy, Am. J. Vet. Res. 47, 236 (1986); A. Lee, et al., Internat. J. System. Bacteriol., 42, 27 (1992); J. L. Penner, In Manual of Clinical Microbiology, A. Ballows, W. J. Hausler, Jr., K. L. Herrmann, H. D. Isenberg, and H. J. Shadomy, Eds. (American Society for Microbiology, Washington, D.C. 1991), PP. 402–409; P. Vandamme, et al. Internat. J. System. Bacteriol. 41, 88 (1991); G. L. Woods, Y. Gutierren, D. H. Walker, D. T. Purtilo, and J. D. Shanley, Eds., Diagnostic Pathology of Infectious Diseases. (Lea & Febiger, Philadelphia, Pa.,1993), pp. 350–356.
2. C. P. Davis, J. S. McAllister, and D. C. Savage, Inf. Imm. 7, 666 (1973);.S. L. Erlandsen, and D. G. Chase, J. Ultrastruct. Res. 41, 319 (1972); H. L. B. M. Klaasen et al., Laboratory Animals 27,141 (1993); A. Lee, J. Gordon, and R. Dubos, Nature 220, 1137 (1968); A. Lee, and M. Phillips, Appl. Environ. Microbiol., 35, 610 (1978);.D. M. M. Queiroz, et al., Laboratory Animals 26, 288 (1992); D. C. Savage, J. S. McAllister, and C. P. Davis, Inf. Imm. 4, 492 (1971); D. B. Shauer, N. Ghori, and S. Falkow, J. Clin. Microbiol., in press.
3. W. Garvey, A. Fathi, and F. Bigelow, J. Histotechnol. 8, 15 (1985).
4. L. M. Anderson, J. P. Carter, D. L. Logsdon, C. L. Driver and K. M. Kovatch, Carcinogenesis, 13, 2107 (1992).
5. K. A. Eaton, et al., Int. J. Syst. Bacteriol. 43, 99 1993); J. G. Fox, et al., Gastroenterology 104, 86, (1993); N. Kusukawa, T. Uemori, K. Asada, and I. Karo, Biotechniques 9, 66 (1990).
6. R. Benveniste, et al., J. Virol. 62, 2091 (1988); U. K. Laemmli, Nature 227, 680 (1970).
7. L. P Anderson and F. Espersen J. Clin. Microbiol. 30, 1743 (1992).
8. Reddy et al. J. Clin. Gastroenterol. 5, 259 (1983).
9. E. Kita, et al, Journal of General Microbiology 132, 3095.(1986); E. Kita, et al., J. Med. Microbiol. 37, 326 (1992); E. Kita, et al., J. Med. Microbiol. 33, 171 (1990)
10. V. J. Desmet, In Oxford textbook of Pathology, J. O. P. McGee, P. G. Isaacson, and N. A. Wright, Eds. (Oxford Univ. Press, Oxford, 1992) pp. 1312–1324; V. M. Arean, Am. J. Pathol. 40, 393 (1962).
11. M. A. Crawford, W. D. Sehall, R. K. Jensen, J. B. Tasker, J. Am. Med. Assoc. 187, 1343 (1985); L. Bishop et al., Am. J. Vet. Res. 40 839, (1979).
12. Archer, J. R., S. Romero, A. E. Ritchie, M. E. Hamacher, B. M. Steiner, J. H. Bryner, and R. F. Schell. 1988. Characterization of an unclassified microaerophilic bacterium associated with gastroenteritis. J. Clin. Microbiol. 26:101–105.
14. Bronsdon, M. A. C. S. Goodwin, L. I. Sly, T. Chilvers, and F. D. Schoenknecht. *Helicobacter nemestrinae* sp. nov., a spiral bacterium found in the stomach of a pigtailed macaque (*Macaca nemestrina*). Int. J. Syst. Bacteriol. 41:148–153 (1991).
Bryner, J. H., A. E. Ritchie, L. Pollet, C. A. Kirkbridge and J. E. Collins. Experimental infection and abortion of pregnant guinea pigs with a unique spirillum-like bacterium isolated from aborted ovine fetuses. Am. J. Vet. Res. 48:91–95 (1987).
15. Dewhirst, F. E., C. Seymour, G. J. Fraser, B. J. Paster, and J. G. Fox. Phylogeny of Helicobacter isolates from bird and swine feces and description of *Helicobacter pametensis* sp. nov. Manuscript in preparation.
16. Eaton, K. A., F. E. Dewhirst, M. J. Radin, J. G. Fox, B. J. Paster, S. Krakowka and D. R. Morgan. *Helicobacter acinonyx* sp. nov., isolated from cheetahs with gastritis. Int. J. Sys. Bacteriol. 43:99–106 (1993).
17. Fennell, C. L., P. A. Totten, T. C. Quinn, D. L. Patton, K. K. Holmes, and W. E. Stamm. Characterization of Campylobacter-like organisms isolated from homosexual men. J. Infect. Dis. 149:58–66 (1984).
18. Foster, J. R. Bacterial infection of the common bile duct in chronic fascioliasis in the rat. J. Comp. Path. 94:175–181 (1984).
19. Fox, J. G. Unpublished observations.
20. Fox, J. G., M. Blanco, J. C. Murphy, N. S. Taylor, A. Lee, Z. Kabok, and J. Pappo. Local and systemic immune responses in murine *Helicobacter felis* active chronic gastritis. Infect. Immun. 61:2309–2315 (1993).
21. Fox, J. G., P. Correa, N. S. Taylor, A. Lee, G. Otto, J. C. Murphy, and R. Rose. *Helicobacter mustelae* associated gastritis in ferrets: an animal model of *Helicobacter pylori* gastritis in humans. Gastroenterology 99:352–361 (1990).
22. Fox, J. G., P. Correa, N. S. Taylor, D. Zavala, E. Fontham, F. Janney, E. Rodriquez, F. Hunter, and S. Diavolitsis. *Campylobacter pylori* associated gastritis and immune response in a population at increased risk of gastric carcinoma. Am. J. Gastroenterol. 89:775–781 (1989).

23. Fox, J. G., B. M. Edrise, E. B. Cabot, C. Beacage, J. C. Murphy, and K. Prostak. Campylobacter like organisms isolated from the gastric mucosa of ferrets. Am. J. Vet. Res. 47:236–239 (1986).

24. Fox, J. G., A. Lee. Gastric helicobacter infection in animals: natural and experimental infections. p. 407–430 (1993). In C. S. Goodwin and B. W. Worsley (eds.) Biology and clinical practice. CRC Press, Boca Raton, Fla.

25. Graham, D. *Campylobacter pylori* and peptic ulcer disease. Gastroenterology 96:615–625 (1989).

26. Jukes, T. H., and C. R. Cantor. 1969. Evolution of protein molecules, p. 21–132. In H. N. Munro (ed.), Mammalian protein metabolism, vol. 3. Academic Press, Inc., N.Y.

27. Kirkbride, C. A., C. E. Gates, J. E. Collins and M. S. Ritchie. Ovine abortion associated with an anaerobic bacterium. J. Am. Vet. Med. Assoc. 186:789–791 (1985).

28. Kita E., F. Nishikawa, K. Kamikaidou, A. Nakano, N. Katsui, S. Kashiba. Mononuclear cell response in the liver of mice infected with hepatotoxenic *Campylobacter jejuni*. J. Med. Micro. 37:326–331 (1992).

29. Kita, E., D. Oku, A. Hamuro, F. Nishikawa, M. Emoto, Y. Yagyu, N. Katsui, and S. Kashiba. J. Med. Microbiol. 33:171–182 (1990).

30. Kusukawa, N., T. Uemori, K. Asada, and I. Kato. Rapid and reliable protocol for direct sequencing of material amplified by the polymerase chain reaction. Biotechniques 9:66–72 (1990).

31. Lee, A., S. L. Hazell, J. O'Rourke, and S. Kouprach. Isolation of a spiral-shaped bacterium from the cat stomach. Infect. Immun. 56:2843–2850 (1988).

32. Marshall, B. J., J. R. Warren. Unidentified curved bacilli in the stomach of patients with gastritis and peptic ulceration. Lancet i:1311–1314 (1984).

33. Nomura, A., G. N. Stemmermann, P. Chyou, I. Kato, G. E. Perez-Perez, M. J. Blaser. Helicobacter infection and gastric adenocarcinoma among Japanese Americans in Hawaii. New Engl. J. Med. 325:1132–1136 (1991).

34. Olsen, G. J., R. Overbeek, N. Larsen, T. L. Marsh, M. J. McCaughey, M. A. Maciukenas, W.-M. Kuan, T. J. Macke, Y. Xing, and C. R. Woese. The ribosomal database project. Nucleic Acids Res. 20:2199–2200 (1992).

35. Parsonnet, J., G. D. Friedman, D. P. Vandersteen, J. H. Chang, J. H. Vogelman, N. Orentriech, R. K. Sibley. *Helicobacter pylori* infection and the risk of gastric adrenocarcinoma. New Engl. J. Med. 325:1127–1131 (1991).

36. Paster, B. J., and F. E. Dewhirst. Phylogeny of campylobacters, wolinelias, *Bacteroides gracilis*, and Bacteroides ureolyticus by 16S ribosomal ribonucleic acid sequencing. Int. J. Syst. Bacteriol. 38:56–62 (1988).

37. Paster B. J., A. Lee, J. G. Fox, F. E. Dewhirst, L. A. Tordoff, G. J. Fraser, J. L. O'Rourke, N. S. Taylor, and R. Ferrero. Phylogeny of *Helicobacter felis* sp. nov., *Helicobacter mustelae*, and related bacteria. Int. *J. Syst. Bacteriol.* 41:31–38 (1991).

38. Phillips, M. W. and A. Lee. Isolation and characterization of a spiral bacterium from the crypts of rodent gastrointestinal tracts. Appl. Environ. Microbiol. 45:675–683 (1983).

39. Romero, S., J. R. Archer, M. E. Hamacher, S. M. Bologna and R. F. Schell. Case report of an unclassified microaerophilic bacterium associated with gastroenteritis. J. Clin. Microbiol. 26: 142–143 (1988).

40. Saitou, N., and M. Nei. The Neighbor-Joining method: new method for reconstructing phylogenetic trees. Mol. Biol. Evol. 4:406–425 (1987).

41. Schauer, D. B., N. Ghori, S. Falkow. Isolation of "*Flexispira rappini*" from mice. J. Clin. Microbiol. 31:2709–2714 (1993).

42. Stanley J., D. Linton, A. P. Burnens, F. E. Dewhirst, R. J. Owen, A. Porter, S. L. W. On, and M. Costas. *Helicobacter canis* sp. nov., a new species from dogs: an integrated study of phenotype and genotype. J. Gen. Microbiol. 139:2495–2504 (1993).

43. Studier, J., and K. Keppler. A note on the Neighbor-Joining algorithm of Saitou and Nei. Mol. Biol. Evol. 5:729–731 (1988).

44. Totten, P. A., C. L. Fennell, F. C. Tenover, J. M. Wezenberg, P. L. Perine, W. E. Stamm, and K. K. Holmes. *Campylobacter cinaedi* (sp. nov.) and *Campylobacter fennelliae* (sp. nov.): Two new Campylobacter species associated with enteric disease in homosexual men. J. Infect. Diseases 151:131–139 (1985).

45. Fox, J. G., Dewhirst, F. E., Tully, J. G., Paster, B. J., Yan, L., Taylor, N. S., Collins, M. J. Jr., Gorelick, P. L. and Ward, J. M.: *Helicobacter hepaticus* sp. nov., a microaerophilic bacterium isolated from livers and intestinal mucosal scrapings from mice. *J. Clin. Microbiol.* 32:1238–1245 (1994).

46. Ward, J. M., M. R. Anver, D. C. Hines, L. M. Anderson, R. J. Russell, J. M. Rice, S. Rahm, M. J. Collins, P. L. Gorelick, M. A. Gonda, and J. C. Donovan. Chronic active hepatitis of unknown origin in mice from a large research facility. Vet. Path. 30:4769 (Abstract) (1993).

47. Wotherspoon, A. C., C. Doglioni, T. C. Diss, P. Langxing, A. Moschini, M. de Boni, P. G. Isaacson. Regression of primary low-grade B-cell gastric lymphoma of mucosaassociated lymphoid tissue type after eradication of *Helicobacter pylori*. Lancet 342:575–577 (1993).

48. Harlow and Lane. *Antibodies: A Laboratory Manual*, Cold Spring Harbor Laboratory, Cold Spring Harbor, N.Y. (1988).

49. Sambrook et al. *Molecular Cloning: A Laboratory Manual*, 2nd. Ed., Cold Spring Harbor, N.Y. (1987).

50. Arnon, R. (Ed.). *Synthetic Vaccines* I:83–92, CRC Press, Inc., Boca Raton, Fla. (1987).

51. Kelly et al. *Bio/Technology 10:163–167* (1992) and Bebbington et al., *Bio/Technology 10:169–175* (1992).

What is claimed is:

1. An isolated *Helicobacter hepaticus* bacterium.

* * * * *